United States Patent [19]
Arthur et al.

[11] Patent Number: 6,004,986
[45] Date of Patent: Dec. 21, 1999

[54] METHOD FOR TREATING CEREBRAL VASOSPASM AND CEREBRAL ISCHEMIA USING IRON CHELATORS AND PHARMACEUTICAL COMPOSITIONS THEREFOR

[75] Inventors: Adam S. Arthur, Salt Lake City, Utah; Giuseppe Lanzino, Charlottesville, Va.

[73] Assignee: The University of Virginia Patent Foundation, Charlottesville, Va.

[21] Appl. No.: 09/074,694

[22] Filed: May 8, 1998

Related U.S. Application Data

[60] Provisional application No. 60/045,947, May 8, 1997.

[51] Int. Cl.⁶ .................................................. A61K 31/44
[52] U.S. Cl. .............................................. 514/348
[58] Field of Search ............................................. 514/348

[56] References Cited

U.S. PATENT DOCUMENTS 4,840,958  6/1989  Hider et al. .
5,789,426  8/1998  Hanauske-Abel et al. .

OTHER PUBLICATIONS

Van Der Kraaij et al, Chemcial Abstracts, vol. 111, abstract No. 90096, 1989.

*Primary Examiner*—William R. A. Jarvis
*Attorney, Agent, or Firm*—Oblon, Spivak, McClelland, Maier & Neustadt, P.C.

[57] ABSTRACT

The invention relates to methods for treating cerebral vasospasm induced by hemorrhage or cerebral ischemia, by treating patients with a therapeutically effective amount of a lipophilic iron chelator.

4 Claims, 2 Drawing Sheets

METHOD FOR TREATING CEREBRAL VASOSPASM AND CEREBRAL ISCHEMIA USING IRON CHELATORS AND PHARMACEUTICAL COMPOSITIONS THEREFOR

CROSS-REFERENCE TO RELATED APPLICATIONS

This application is a regular National application claiming priority from Provisional Application, U.S. application Ser. No. 60/045,947 filed May 8, 1997.

BACKGROUND OF THE INVENTION

1. Field of the Invention

The present invention relates to a method for treating cerebral vasospasm and/or cerebral ischemia using iron chelators. More particularly, the present invention relates to a method for treating cerebral vasospasm by administering to a patient an iron chelator which is able to cross the blood-brain barrier.

2. Description of Related Art

Although there are several postulated mechanisms for cerebral vasospasm, there is evidence supporting oxyhemoglobin as the principal spasmogen. Furthermore, recent experiments indicate that the binding properties of iron as a catalytic transitional metal play an important role early in the reaction cascade.

During erythrocyte lysis, free iron is released and accumulates in the cerebrospinal fluid (CSF) in the absence of iron binding proteins (e.g., transferrin. Additionally, oxyhemoglobin is released and auto-oxidizes to form methemoglobin and superoxide radicals. Free iron interacts with superoxides in the Fenton reaction and leads to the formation of hydroxyl radicals. Hydroxyl radicals are extremely reactive and initiate several cascade reactions, including lipid peroxidation, that can lead to cellular injury. (Kassell et al, J Neurosurg 73:18–36, 1990)

Limiting the amount of iron available to catalyze the Fenton reaction results in decreased free radical formation. (Al Refaie et al, Blood 80:593–599, 1992) It has been demonstrated that iron chelation with deferoxamine is effective in attenuating vasospasm. (Comair et al, Neurosurgery 32:58–65, 1993; Kontoghiorghes, Indian J Pediatr 60(4):485–507, 1993) Deferoxamine, a chelator of intra- and extracellular iron, is cytoprotective in several models of tissue injury and has been shown to protect against cerebral vasospasm in vivo. (Comair et al, Neurosurgery 32:58–65, 1993; Hamilton et al, Brit J Haem 86:851–857, 1994; Kontoghiorghes et al, Indian J Pediatr 60(4):485–507, 1993) However, although deferoxamine is effective as an iron chelator, it is relatively hydrophilic and thus does not readily cross lipid bilayers. Such hydrophilic compounds are therefore not as effective for treating cerebral vasospasm, because they cannot cross the blood-brain barrier.

Cerebral ischemia, commonly stroke, is one of the largest causes of morbidity and mortality in the United States. In this medical crisis, brain tissue is deprived of blood. In such a situation, the generation of harmful superoxide radicals may be responsible for a significant amount of damage to brain tissue. Effective suppression of these harmful radicals may protect against at least some of the nerve cell damage encountered in stroke patients.

Therefore, in view of the aforementioned deficiencies attendant with prior art methods of treating cerebral vasospasm and cerebral ischemia, it should be apparent that there still exists a need in the art for method for such treatment.

SUMMARY OF THE INVENTION

Accordingly, one object of this invention is to provide a novel material and pharmaceutical composition for treatment of cerebral vasospasm and cerebral ischemia.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
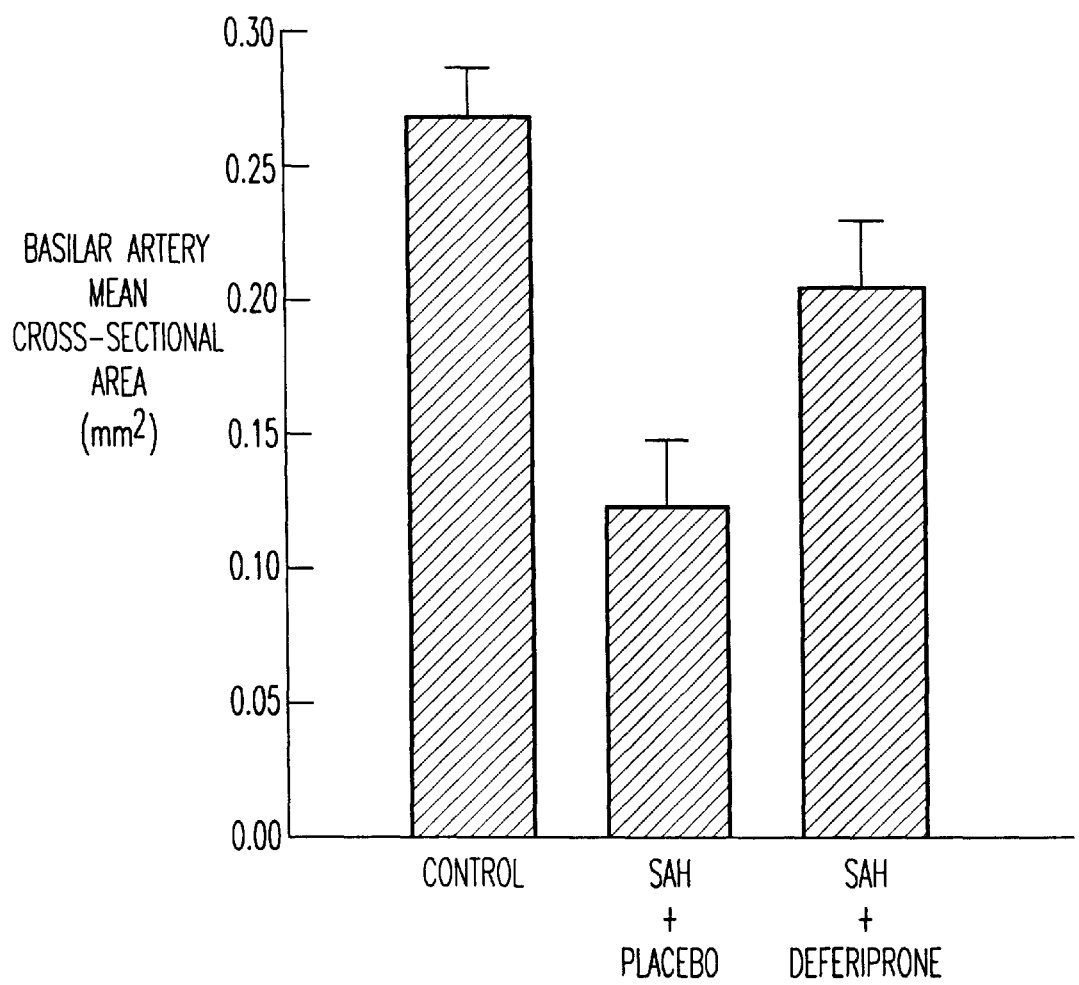
FIG. 1 is a graphical representation of the mean values of cross-sectional area values of the basilar artery lumen showing the effect of deferiprone on cerebral vasospasm in rabbits.

The present inventors have now found that iron chelators which are hydrophobic in nature, are able to cross the blood-brain barrier (BBB) and are effective at inhibiting cerebral vasospasm. The issue of BBB penetration is a complex one. Theoretical measurements include the delta-delta value, a measure of the differential solubility in octane and octanol. For simplicity, the lipid-water partition coefficient is employed in this application. A preferred hydrophobic chelator for use in accordance with the present invention is deferiprone. Deferiprone, in contrast to deferoxamine, is highly lipophilic. A variety of similar compounds, developed for other purposes, are known. 21-aminosteriods, such as those set forth in U.S. Pat. No. 4,975,537, may be used in this invention. Deferiprone, (1,2-dimethyl-3-hydroxypyrid-4-one) has a lipid-water partition coefficient 21 times greater than deferoxamine. In general, a chelator effective in this invention should have a lipid-water partition coefficient at least 10 times that of deferoxamine.

The preferred iron chelating compounds to be used in accordance with the method of this invention, as active agents in the pharmaceutical compositions of this invention, are substituted hydroxypyridines. Deferiprone (1,2-dimethyl-3-hydroxypyrid-4-one) has the structure

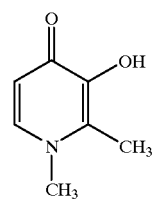

In general, the methyl groups of deferiprone may be substituted for with bulky alkyl groups, particularly to improve lipophilicty. Accordingly, preferred compounds for use in this invention as active agents in the pharmaceutical compositions for administration to those in need of treatment for cerebral vasospasm or cerebral ischemia are compounds of the formula

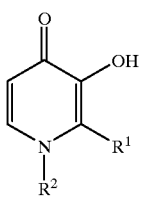

where $R^1$ and $R^2$ are independently linear or branched alkyls of 1–12 carbon atoms, preferably 1–6 carbon atoms, or hydrogen, with the proviso that at least one of $R^1$ and $R^2$ is not hydrogen. Particularly preferred compounds are those wherein both $R^1$ and $R^2$ are alkyl compounds, with further preference being had for substituents such as t-butyl groups. In a preferred embodiment, $R^1$ is methyl and $R^2$ is t-butyl.

As used herein, the phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce a feature or pathology attendant with cerebral vasospasm, such as for example, cross-sectional area of the basilar artery and corrugation of the internal elastic lamina, or to suppress formation of tissue damaging free radicals. Clinical cerebral vasospasm is typically detected functionally as it causes delayed ischemia neurologic deficits (DINDS). It can also be detected by angiography or Doppler measurement of blood velocities.

The active agent of the invention may be prepared in pharmaceutical compositions, with a suitable carrier and at a strength effective for administration by various means to a patient experiencing an adverse medical condition associated with cerebral vasospasm for the treatment thereof. A variety of administrative techniques may be utilized, among them, oral administration, parenteral techniques such as subcutaneous, intravenous and intraperitoneal injections, catheterizations and the like. Average quantities of the iron chelator may vary and in particular should be based upon the recommendations and prescription of a qualified physician or veterinarian.

The preparation of therapeutic compositions which contain active ingredients is well understood in the art. Typically, such compositions are prepared as oral consumables or injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

The iron chelators can be formulated into the therapeutic composition as neutralized pharmaceutically acceptable salt forms. Pharmaceutically acceptable salts include the acid addition salts and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle. Suitable ranges for a unit dose are 30 to 300 mg/kg, preferably 100 to 200 mg/kg, and more preferably 150 to 200 mg/kg.

The compositions are administered in a manner compatible with the dosage formulation, and in a therapeutically effective amount. The quantity to be administered depends on the subject to be treated, capacity of the subject's immune system to utilize the active ingredient, and degree of iron chelation desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to 100 micromolar in the blood are contemplated.

The therapeutic compositions may further include an effective amount of the iron chelator, and one or more of the following active ingredients: an antibiotic, a steroid.

The substituted pyridone deferiprone is an iron chelator that has a partition coefficient 21 times that of deferoxamine. Recent work shows that the cellular uptake of deferiprone is significantly higher than that of deferoxamine. (Berdoukas et al, Lancet 341:1088, 1993) Other studies have shown that deferiprone, unlike deferoxamine, is able to chelate transferrin-derived endosomal iron. (Gale et al, Res Comun Chem Pathol Pharmacol Vol. 73, No. 3, September 1991) Deferiprone's ability to dramatically decrease lipid peroxidation, hydroxyl radical production, and free radical-mediated cell damage has been well documented. (Kamiyama et al, Neurol Med Chir 21:201–209, 1981). A recent paper has also demonstrated that deferiprone can penetrate into both ventricular CSF and cortical brain tissue less than seven minutes after systemic administration. (Asano et al, Wilkins RH (ed) 190–201, 1980)

Additionally, in a clinical setting, deferiprone may act as a neuroprotective agent since oxygen free-radical production has been causally linked to ischemic-mediated neuronal destruction.(Sasaki et al, J Neurosurg 54:357–365, 1981). This assertion is supported by recently published work showing that deferiprone is effective in reducing ischemic damage to canine spinal cord following experimental arterial occlusion.(Reuter et al, J Thorac Cardiovasc Surg 109(5):1017–1019, 1995) In addition, deferiprone may be effective in decreasing the infarct volume in a rat model of temporary focal cerebral ischemic. Accordingly, treatment of both cerebral vasospasm and cerebral ischemia are contemplated within the scope of this invention. As there are no known significant side-effects to the short term administration of the preferred substituted pyridones of this invention, routine "protective" doses of the pharmaceutical compositions may be administered whenever strokes are suspected to have occurred.

Although not intending to be bound by theory, the following lines of evidence support the hypothesis that the protective effect of deferiprone results from the iron-binding capacity of the compound and from the prevention of free radical production: 1) deferiprone's effect is not mediated by a direct vasodilatory action on vessel tone since administration of the compound to non-SAH rabbits (Group 4 in this study) did not produce a change in vessel size; 2) deferiprone's ability to dramatically decrease lipid peroxidation, hydroxyl radical production, and free radical-mediated cell damage has already been established (e.g. Morel et al.), and 3) deferiprone's well-characterized binding properties are very similar to those of deferoxamine and the 21-aminosteroids which have been extensively studied in cerebral vasospasm.(Comair et al, Neurosurgery 32:58–65, 1993; Harada et al, J Neurosurg 77:763–767, 1992; Morel et al, Free Radic Biol Med 13:499–508, 1992; Sano et al, Neurol Res 2:253–272, 1980, Vollmer et al, Neurosurgery 28:27–32, 1991)

Preferred substituted pyridones such as deferiprone are attractive candidates for clinical therapy because of this rapid absorption, high lipid solubility, low incidence of serious side effects, and documented ability to chelate iron and prevent the production of free-radical species. The present findings provide a clear indication that this iron chelator can be of benefit for the treatment of cerebral vasospasm following SAH.

Deferiprone and related compounds have been shown to be safe for administration in humans, with few side effects. (Fassos et al, Clin Pharmacol Ther 55:70–75, 1994; Hider et al, U.K. Patent GB-2118176; Harada et al, J Neurosurg 77:763–767, 1992; Harada et al, J Neurosurg 77:763–767, 1992; Agarwal et al, Br J Haematol 82:460–466, 1992; Kontoghiorghes et al, Ann N Y Acad Sci 34:339–350, 1992) Deferiprone, unlike deferoxamine, has been shown to rapidly penetrate the intracellular environment and to chelate endosomal stores of iron.

Having generally described this invention, a further understanding can be obtained by reference to certain specific examples which are provided herein for purposes of illustration only and are not intended to be limiting unless otherwise specified.

EXAMPLES

Twenty-eight male New Zealand White rabbits were assigned to one of four groups (Table 1). Rabbits in the subarachnoid hemorrhage (SAH) groups were sacrificed 48 hours after they were subjected to SAH. Group 1 (Control) was not subjected to SAH or administered any treatment (n=8). Group 2 (SAH+placebo) was subjected to SAH and given an oral placebo (n=8). Group 3 (SAH+deferiprone) was subjected to SAH and given oral administration of deferiprone (n=8) while Group 4 (deferiprone only) was not subjected to SAH but was given deferiprone (n=4).

TABLE 1

ADMINISTRATION SCHEDULE*

| Observation Period | 0 hrs | 8 hrs | 16 hrs | 24 hrs | 32 hrs | 40 hrs | 48 hrs |
|---|---|---|---|---|---|---|---|
| Group 1 (Control) | | | | | | | F |
| Group 2 (SAH + Placebo) | SAH | P | P | P | P | P | F |
| Group 3 (SAH + Deferiprone) | SAH | D | D | D | D | D | F |
| Group 4 (Deferiprone Only) | | D | D | D | D | D | F |

*SAH = induction of subarachnoid hemorrhage
P = administration of placebo
D = administration of 100 mg/kg deferiprone
F = sacrifice by perfusion-fixation The techniques utilized for SAH, perfusion-fixation, embedding, and morphometry were performed as described previously (Takahashi et al, Neurosurgery 32(2):281–288, 1993), and are described below.

Deferiprone was synthesized as described previously. (Gale et al, Res Comun Chem Pathol Pharmacol Vol. 73, No. 3, September 1991) An aqueous suspension of 3-hydroxy-2-methyl-pyrone, maltol, (Aldrich Chemical Co., Milwaukee, Wis., 50 gm, 396 nmol) and $NH_2CH_3$ (Aldrich Chemical Co., Milwaukee, Wis., 3 eq, 92 ml, 1.18 mol, 12.88 M) in distilled, degassed $H_2O$ was heated under reflux for 12 hours. The solution was allowed to cool to room temperature. The excess methyl amine was removed under reduced pressure and the brown mixture was carefully concentrated to a volume of approximately 200 ml. Reagent grade acetone (50 ml) was added to this brown suspension and the solid recovered by filtration. The solid was washed with 1200 ml of acetone and briefly allowed to dry. To this crude solid was added 2 g of Norite and 2 g of Celite 545 (fisher Scientific, Pittsburgh, Pa.) and the crude solid was dissolved in a minimal amount of hot water. The Celite/Norite matrix was removed from the solution by filtration. The pure crystalline compound was recovered by filtration to give 29.8 g (54%) of the title compound. All recovery and transfer procedures were performed with a porcelain spatula rather than stainless steel equipment due to the potent iron chelating property of 1,2-dimethyl-3-hydroxypyrid-4-one. Analytically pure 1,2-dimethyl-3-hydroxypyrid-4-one was obtained by a single recrystallization from $H_2O$. Other alkyl-substituted pyridones can be prepared by similar measures.

Analytical Data: $R_f$ 0.25 (1:1, EtOAC:Pet. Ether); m.p. 269–70° C. uncorrected; $^1H$ NMR ($H_2O$, 300 MHZ) 2.35 (s,3H, vinylic —$CH_3$), 3.71 (s, 3H, N—$CH_3$), 6.49 (d, 1H, vinylic H@C6, J=7.1 Hz), 7.98 (d, 1H, vinylic H@C51, J=7.1 Hz); $^{13}C$ NMR ($H_2O$, 75 MHZ) 12.25, 42.61, 112.49, 139.38, 142.99, 153.6)

The administration schedule for each of the four experimental groups during the 48 hour study period is shown in Table 1. Deferiprone (100 mg/kg) in gel capsules was administered to Groups 3 and 4 every 8 hours per os. Dosing began 8 hours after SAH in Group 3, and 8 hours after initial observation in Group 4. The last dose was administered at hour 40 of the study period (i.e. 8 hours prior to sacrifice) for a total of 5 doses. Experimental animals in Group 2 (SAH+placebo) were dosed with empty gel capsules using the same administration schedule.

Animals in Groups 2 and 3 were anesthetized with an intramuscular injection of a mixture of ketamine (40 mg/kg) and xylazine (8 mg/kg) and endotracheally intubated. The central ear artery was cannulated to obtain 5 cc of autologous arterial blood. A 23 gauge butterfly needle was inserted percutaneously into the cisterna magna and the 5 cc of autologous blood was injected over a 10 second period. The animals were then positioned with their heads down for 20 minutes to facilitate the settling of blood in the basal cisterns. The animals were monitored closely for respiratory distress and were immediately placed on a ventilator. They remained on the ventilator until spontaneous respiration resumed. The animals were extubated and returned to their cages when fully awake. The animals were given free access to food and water over the next 48 hours and were observed closely for poor feeding or any possible neurological deficits.

Animals were anesthetized at the 48$^{th}$ hour of the study period as described above; they were then intubated, ventilated and paralyzed with pancuronium bromide (0.3 mg/kg). The central ear artery was cannulated for recording arterial pressure via an arterial line transducer. Arterial blood gas tensions were measured and ventilation parameters adjusted accordingly to maintain arterial $pO_2$ and pCO within the physiological range. After satisfactory respiratory parameters under anesthesia were established, the thorax was opened and a cannula was placed in the aorta via the left ventricle. The right atrial appendage was opened and the descending thoracic aorta was clamped. The vascular system was perfused with 300 ml of Hanks' balanced salt solution (Sigma Chemical Co., St. Louis, Mo.) (pH 7.4 at 37° C.) followed by 500 ml of 1% paraformaldehyde and 1.5% glutaraldehyde fixative in Hanks' balanced salt solution (pH 7.4 at 37° C.). Perfusion was performed at a pressure of 75 mm Hg in all groups. After perfusion-fixation, the brainstem was removed, placed in the same fixative solution, and stored at 4° C. overnight. Animals that showed incomplete subarachnoid clot, or had residual blood in the vasculature suggesting an inadequate perfusion were excluded from the study at this point.

After fixation, the basilar artery was removed from the brainstem and the proximal third of the vessel was cut into segments 2 mm in length. The tissue samples were washed several times in 0.1 mol/L phosphate buffer, postfixed in 1% osmium tetroxide in 0.1 mol/L phosphate buffer (pH 7.4) for 1 hour at room temperature, and then washed again in phosphate buffer. The tissue was dehydrated through a series of graded ethyl alcohol solutions followed by propylene oxide. The samples were placed into a 1:1 mixture of propylene oxide and epoxy resin overnight, and then flat embedded the next day in 100% epoxy resin and allowed to polymerize at 60° C. for 48 hours. Cross-sections of the basilar artery (0.5 μm thick) were cut on a Reichert Ultracut E ultramicrotome (Vienna, Austria), mounted on glass slides, and stained with toluidine blue for light microscopy.

Morphometric measurements of three randomly selected arterial cross-sections from each animal were performed using the Image 1 Analysis System (Universal Imaging, West Chester, Pa.). Basilar artery cross-sectional area of the basilar artery lumen was measured by an investigator blinded to the treatment groups of the individual arteries. Three measurements were taken from randomly selected cross-sections of each basilar artery. The luminal area for each basilar artery was obtained by averaging these 3 measurements.

A Kruskal-Wallis one-way ANOVA was performed on the entire data set which showed a significance of 0.0048. Direct comparison of treatment groups was performed using a one-tailed Mann-Whitney U test.

One animal from Group 4 (deferiprone only) was found to have residual blood in the cerebral vasculature following perfusion-fixation and was excluded from the study. No animals in any of the treatment groups were observed to have any neurological deficits or to be feeding poorly.

Cross-sectional area values are shown in Table 2 and a graphical representation of the mean values of each group is presented in FIG. 1. Subarachnoid hemorrhage elicited a reduction in vascular area of 54% in the placebo-treated animals (Group 2). In contrast, the reduction in cross-sectional area in animals treated with deferiprone was only 24%; this represents a statistically significant attenuation of the vasospastic response observed in Group 2. It is also noteworthy that although the cross-sectional area of vessels in the SAH+deferiprone group (Group 3) animals was less than that for control animals, this difference did not achieve statistical significance. Finally, the values obtained for animals treated with deferiprone but not subjected to SAH (Group 4) did not differ from the untreated control animals (Group 1).

TABLE 2

| CROSS-SECTIONAL AREA OF BASILAR ARTERIES | | | |
|---|---|---|---|
| Group 1: Control | Group 2: SAH + Placebo | Group 3: SAH + Deferiprone | Group 4: Deferiprone Only |
| 2.832 | 2.017 | 1.830 | 3.100 |
| 3.134 | 0.866 | 2.818 | 3.303 |
| 3.210 | 0.808 | 0.739 | 2.070 |
| 2.918 | 0.666 | 2.217 | |
| 2.542 | 0.904 | 2.124 | |
| 2.181 | 2.699 | 1.370 | |
| 3.166 | 0.917 | 2.749 | |
| 1.746 | 1.130 | 2.817 | |
| 2.72 ± 0.19*# | 1.25 ± 0.25# | 2.08 ± 0.26 | 2.82 ± 0.38 |

All values are expressed in units of $10^5$ μm$^2$.
*$P < 0.005$ compared to Group 2.
$P < 0.05$ compared to Group 3.

Figure 2A:
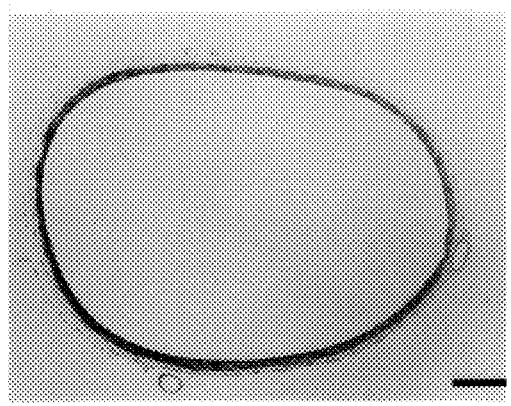
FIG. 2 depicts representative arterial cross-sections from each of the study groups.
Figure 2B:
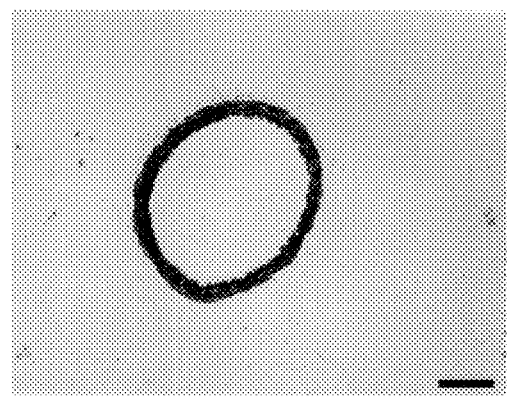
Figure 2C:
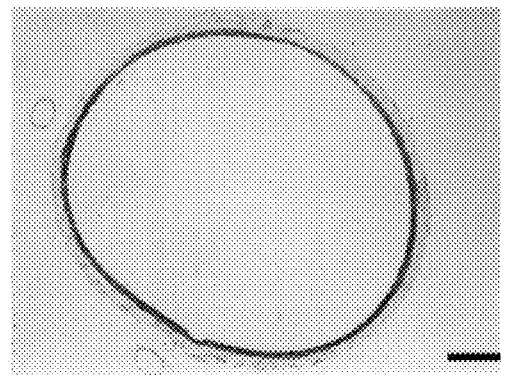

FIG. 2 depicts representative arterial cross-sections from each of the study groups. Vasospasm was evident in Group 2 (SAH+placebo) (FIG. 2B) in which characteristic corrugation of the internal elastic lamina (IEL) was observed. Group 1 (Control) (FIG. 2A) and Group 4 (deferiprone only) did not demonstrate any evidence of vasospasm on histological evaluation. Animals in Group 3 (SAH+deferiprone) (FIG. 2C) showed a variable amount of corrugation of the IEL; in all instances, this corrugation was qualitatively less than that observed in Group 2 (SAH+placebo).

The dosage of deferiprone used in this study was approximately one tenth of the LD50 dosage reported in the literature but was roughly twice the dosage administered to most of the human subjects receiving long-term deferiprone. (Agarwal et al, Br J Haematol 82:460–466, 1992; Berdoukas et al, Lancet 341:1088, 1993; Kontoghiorghes et al, Indian J Pediatr 60(4):485–507, 1993; Kontoghiorghes et al, Clin Pharm Ther 34:255–261, 1990; Tondury et al, Br J Haematol 76:550–553, 1990) Since cerebral vasospasm typically occurs between days 3–21 after SAH with a peak at day 10, deferiprone could be safely administered prophylactically in the clinical setting following the onset of SAH or suspected cerebral ischemia without encountering any of the side effects associated with long-term deferiprone usage.(Kassell et al, J Neurosurg 73:18–36, 1990)

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method for treating cerebral vasospasm or cerebral ischemia, comprising administering to a patient in need thereof a therapeutically effective amount of an active agent of the formula:

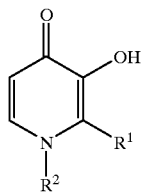

wherein $R^1$ and $R^2$ are independently C1–12 branched or linear alkyl or hydrogen, with the proviso that both $R^1$ and $R^2$ are not hydrogen.

2. The method of claim 1, wherein both $R^1$ and $R^2$ are methyl.

3. The method of claim 1, wherein $R^2$ is t-butyl and $R^1$ is methyl.

4. The method of claim 1, wherein said active agent is administered within 24-hours of (1) a hemorrhage in the patient's brain or (2) a cerebral ischemia event.

* * * * *